United States Patent [19]
Pages

[11] Patent Number: 4,943,273
[45] Date of Patent: Jul. 24, 1990

[54] DISPOSABLE CENTRIFUGE BOWL FOR BLOOD PROCESSING

[75] Inventor: Etienne Pages, Divonne, France

[73] Assignee: Haemonetics Corporation, Braintree, Mass.

[21] Appl. No.: 294,056

[22] Filed: Jan. 5, 1989

Related U.S. Application Data

[63] Continuation-in-part of Ser. No. 232,544, Aug. 15, 1988, which is a continuation of Ser. No. 888,764, Jul. 22, 1986.

[51] Int. Cl.⁵ .............................................. B04B 7/00
[52] U.S. Cl. ........................................ 494/41; 494/64
[58] Field of Search .................. 494/37, 38, 40, 41, 494/48, 60, 64, 65, 80, 73, 76, 77, 78; 604/4, 6

[56] References Cited

U.S. PATENT DOCUMENTS

| | | | |
|---|---|---|---|
| 764,489 | 7/1904 | McLeod | 494/77 |
| 825,721 | 7/1906 | Hartmann | 494/77 |
| 4,059,108 | 11/1977 | Latham, Jr. | 128/214 R |
| 4,086,924 | 5/1978 | Latham, Jr. | 128/214 R |
| 4,204,537 | 5/1980 | Latham, Jr. | 128/214 R |
| 4,300,717 | 11/1981 | Latham, Jr. | 233/1 A |

*Primary Examiner*—Robert W. Jenkins
*Attorney, Agent, or Firm*—Hamilton, Brook, Smith & Reynolds

[57] ABSTRACT

An improved disposable blood processing centrifuge bowl is described comprising a rotary seal enclosing an aperture in a bowl body through which a two-piece core assembly is inserted.

10 Claims, 2 Drawing Sheets

DISPOSABLE CENTRIFUGE BOWL FOR BLOOD PROCESSING

RELATED APPLICATIONS

This application is a continuation-in-part of U.S. patent application Ser. No. 07/232,544 filed 8/15/88 entitled "Plasmapheresis Centrifuge Bowl" to Thomas D. Headley, which is a continuation of U.S. patent application Ser. No. 06/888,764 filed 7/22/86 entitled "Plasmapheresis Centrifuge Bowl" to Thomas D. Headley.

TECHNICAL FIELD

This invention relates to blood processing and, more specifically, centrifuge bowls for blood processing.

BACKGROUND OF THE INVENTION

Disposable centrifuge bowls have been developed for processing anticoagulated whole blood in pheresis and cell washing procedures. Prior to about 1986, commercially available disposable blood processing centrifuge bowls were of the type generally shown in FIGS. 1 or 6 of U.S. Pat. No. 4,300,717 (hereinafter "Latham bowl"), or U.S. Pat. No. 4,086,924 (hereinafter "Grenade bowl"). The overall bowl construction in each case was similar and consisted of three essential units. The first was a multi-piece feed tube and seal assembly, which enable anticoagulated whole blood and/or wash solution to be introduced to the interior of a rotating bowl body from a fixed location, and processed blood component to be removed from the bowl body and returned to a patient or donor, or stored. The second unit comprised a two-piece bowl body welded together at a peripheral seam.

The third unit was a core body usually of fairly solid construction. The core body served a number of functions. In the Latham bowl, it provides a narrow bottom fluid channel between the base of the core and the bottom of the bowl, through which fluid admitted through a central feed tube was passed to the outer periphery of the bowl body interior. In passing through this narrow channel, "impeller" vanes, formed on the bottom of the bowl, impart rotational velocity to the incoming feed fluid. With the core design shown in the Latham bowl, fluid feed is forced to pass to the outer separation region between the inner peripheral bowl body wall and the outer peripheral wall of the core. Without this core design, it would be possible for fluid admitted at the bottom of the bowl to by-pass the separation region and pass directly from the feed tube upwardly through the space between the inner core wall and the feed tube out the effluent port formed between the skirts of the seal assembly. The rigid core body was considered essential to avoid or dampen fluid wave vibrations which might occur between the rotating sterile air in the central region between the core and the feed tube and the fluid processed in the outer separation region.

The Grenade bowl construction is similar, except that the middle bowl body side walls are not tapered and the bottom of the core is not flared.

In addition to the above designs, a pheresis bowl, which was never commercialized, is described in U.S. Pat. No. 4,059,108. This bowl was of two-piece construction, formed of a lower red cell reservoir and a plasma with a core baffle system (shown in FIG. 18) for the red cell reservoir.

Sometime during 1986/87, a new centrifuge bowl became commercially available. The construction of this bowl is shown in the FIG. 4-6 embodiment of copending U.S. Pat. application Ser. No. 07/232,544 filed 8/15/88, which is a continuation of Ser. No. 888,764 filed 7/22/86. This new bowl differed from the prior art bowl by the use of a one-piece integral blow molded bowl body. Among other things, this construction (hereinafter "integral bowl") eliminated the need for a weld about the periphery of the bowl; a possible source of bowl failure at high centrifugal speeds.

The FIG. 4-6 embodiment of the integral bowl utilized a one-piece core body with an outer diameter is equal to or smaller than the opening into the bowl. The small core size is insufficient to enable the core to force feed fluid, entering the bottom of the bowl through the feed tube, to be diverted to the extreme outer periphery of the separation region between the core body and the bowl wall. This diversion is extremely important for cell washing procedures.

In cell washing systems, shed blood from a patient is filtered, collected and washed with saline in a disposable centrifuge bowl. Anticoagulated, filtered shed whole blood enters at the bottom center of the bowl and is separated by centrifugal forces into more dense red cells and less dense other components. The red cells fill the outermost portion of the rotating centrifuge bowl. As more shed blood enters the bowl, the red cells remain in the bowl displacing the supernatant (saline, plasma, contaminants, etc.) out of the mid-central region of the bowl. This concentrates the red blood cells in the bowl. Next, saline is directed into the bottom of the bowl, instead of shed blood. Saline, entering the Latham bowl, is directed by the lower extended skirt portion of the core to the outermost radius of the bowl and through the bed of packed red blood cells. In this way, the supernatant is diluted and displaced by the saline until a satisfactory "washout" efficiency is obtained.

The term "washout" efficiency, sometimes referred to as merely "washout", denotes the percentage of non-red blood cell fluid, i.e., plasma and saline and contaminants, originally entering the bowl and which are removed by the wash process. A 90% or greater efficiency is typically the goal of the wash process. At the end of the "wash" cycle, the contents of the bowl are red cells suspended in saline. The centrifugal washing procedure in conjunction with filtration concentrates the red blood cells and removes contaminants, such as blood clots, bone chips, fatty tissue and activates clotting factors. The patient can then be reinfused with his or her own washed red blood cells.

The FIG. 4-6 embodiment of the integral bowl body bowl of the parent application does not disclose a diverter structure, as in the Latham type bowl. Therefore, some of the saline wash solution may not be forced to travel through the packed red cells before exiting the bowl through the effluent skirts on the rotary seal. This substantially decreases the washout efficiency and, hence, the time it takes to complete a cell washing procedure. As might be expected, time is an extremely critical factor in cell washing procedures, both from the point of view of cost and patient comfort and safety.

DISCLOSURE OF THE INVENTION

In alternate embodiments of the integral bowl patent application, two core structures are disclosed which permit use of an integral bowl body, yet enable the core diameter to exceed the diameter of the bowl body opening. In one embodiment, the core is formed of one-piece construction using semi-rigid plastic material with a flared core and a wall body which can be deflected to allow the flared core to be inserted through the smaller diameter opening. This one-piece core construction, shown in cross-section in FIG. 7 of the parent application, is complex and would be difficult and expensive to fabricate. Also, since it is unsecured along its length, it is susceptible to lateral movement in the event of vibrations which could occur as fluid in the bowl is rotated. Such lateral movement may result in blockage of the channel between the bottom flange of the core and the angled bottom wall of the bowl.

In the FIG. 9-10 embodiment of the parent application, the core is of two-piece construction. One piece is comprised of a generally cylindrical hollow walled core. The other piece is a disc-like member with a flared wall portion adapted to be located adjacent the diagonal wall of the bowl body.

The disc-like member is made of semi-rigid plastic and can be compressed to allow it to pass through the top opening in the bowl body. Circular grooves are formed around protrusions on the member to permit the bottom of the cylindrical core wall to made with the member after the walled core is inserted into the bowl body. The circular grooves form a press-fit, holding the two pieces together during rotation of the bowl. A central aperture in the disc-like member permits whole blood from a feed tube stem to enter the bottom of the bowl body.

This two-piece embodiment is difficult to assemble in the bowl body, relies on a press fit with very little penetration between the mating members, and is also subject to vibrational displacement since the length of the core is essentially suspended from the top without lateral support.

The above summary of the development of centrifuge bowls over a long period of time reveals a need for a core body for blood processing centrifuge bowls which can be used in integral bowl bodies or non-integral bowl bodies, yet retain the features of the Latham style bowl, especially in connection with cell washing protocol. It would also be desirable to have a core body which could be constructed such that the same core body could be utilized for bowls of various volumetric sizes.

The method and apparatus of the present invention comprises, in general, a disposable centrifuge rotor or bowl formed of a combination of three basic items. The first is a rotary seal and header assembly; the second, a bowl body, preferably of seamless, integral, one-piece construction and the third is a two-piece core assembly capable of being rigidly retained against a bowl wall and used in standard bowl bodies of different internal volumetric capacity. The seal and header assembly is as described in the above-referenced parent application. The bowl body is preferably adapted to be manufactured by blow molding or injection blow molding, as also described in the parent application.

The core assembly consists of two plastic pieces made by injection molding or similar processes. The first piece is a generally cylindrical rigid hollow-walled core, similar to the walled core in the parent application. The second piece is a diverter in the form of a semi-rigid donut-like member, scalloped at its peripheral edges and having an outer diameter greater than the bowl opening and about equal to the inner diameter of the mid-section of the bowl.

An inner hole is provided on the donut-like member. This hole has a diameter slightly smaller than the diameter of the effluent header.

The core assembly is assembled inside the bowl by first bending the diverter to permit it to fit inside the bowl and then bending it back to its original flat aspect to fit laterally and horizontally across the bowl body. The walled core is then inserted through the bowl opening. The longitudinal length of the core is sized to be just long enough so that when the core is pushed downwardly in the bowl, it pushes the diverter downwardly into the bowl, also, until the diverter is laying in a generally horizontal, slightly bowed, rigid, compressed position opposite that portion of the bowl body which begins to incline radially inwardly and downwardly and become conical.

Optionally, a ring of holes are provided on the diverter with the ring concentric to the inner hole in the diverter and the diameter of the ring and hole size such that the holes in the ring are located slightly radially outwardly from the core wall. These holes enable subsequent feed fluid to be introduced to the separation region at a radially inward bottom location after the initial introduction of fluid has occurred and separated component begins to block the peripheral scalloped openings.

The vertical location of the diverter can be adjusted for different volumetric bowl capacities simply by changing the length of the core wall. The semi-rigid diverter is held in compression against the inner circumferential side wall of the bowl body and is, therefore, less susceptible to movement caused by vibration or turbulence when the bowl is rotated at high speeds.

The above and other features and advantages will now be described in detail in connection with the drawings.

BEST MODE OF CARRYING OUT THE INVENTION

Figures 1, 2:
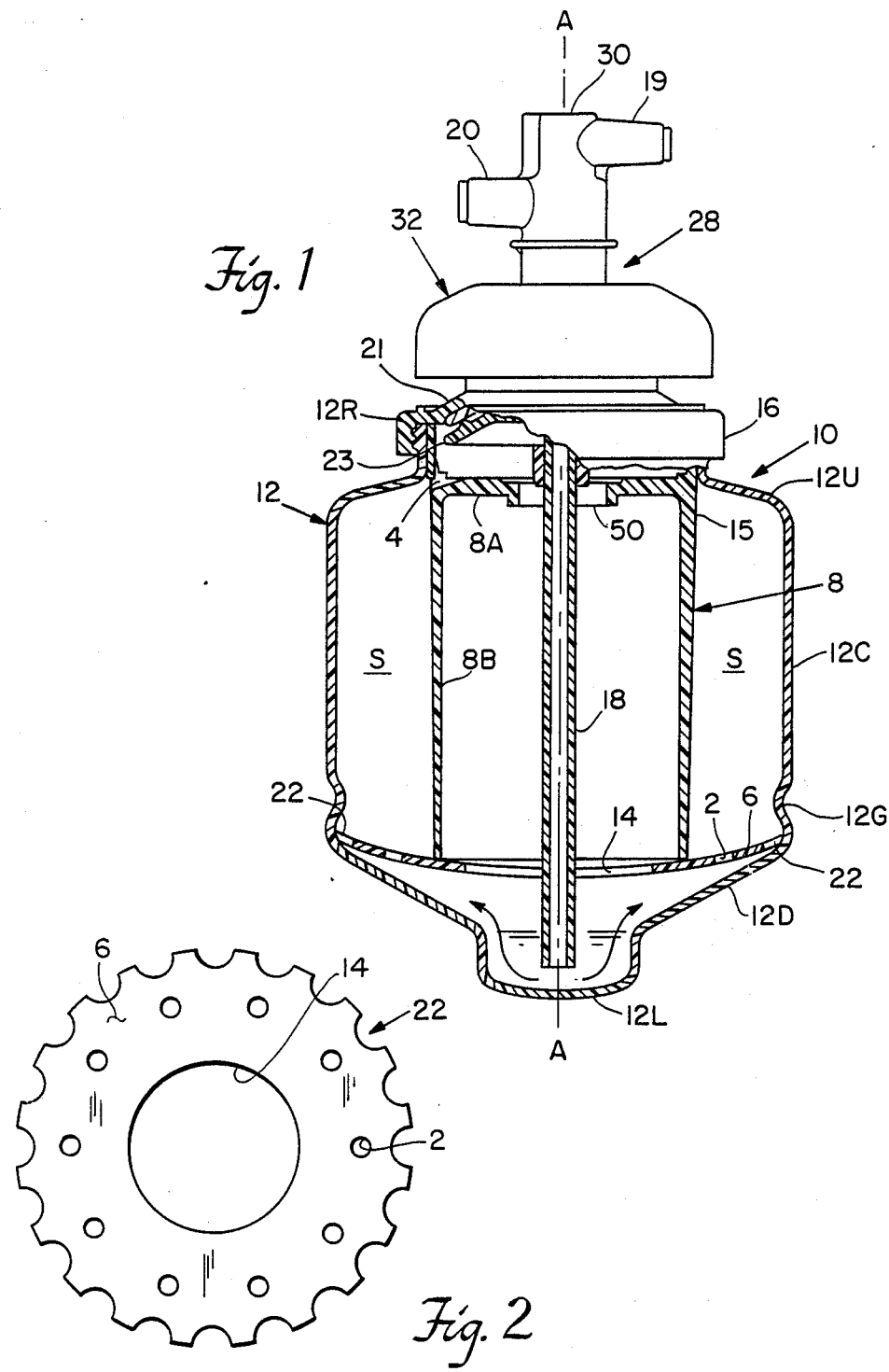
FIG. 1 is a cutaway side view showing a centrifuge bowl of the present invention with the core construction shown in cross-section.
FIG. 2 is a top view of the diverter 10 of FIG. 1 in accordance with the invention.

Referring now to FIGS. 1-2, the apparatus of the invention will now be described in detail in connection with an integral bowl body cell washing process. It is emphasized that the method and apparatus of the invention is capable of general applicability to other blood processing methods, such as pheresis, and to other bowl body structures.

As shown therein, the centrifuge rotor or bowl 10 of the invention, comprises a seal and header assembly, shown generally at 28; a one-piece integral bowl body, shown generally at 12; and a core assembly comprising core body 8 and diverter 6.

The seal and header assembly 28 is substantially identical to the seal and header assembly utilized in the parent application referenced above. Therefore, it need not be described in detail herein. Briefly, the assembly 28 is comprised of a non-rotatable header 30, an effluent tube (not shown), a feed tube assembly (not shown) and a rotary seal formed beneath secondary shield 32 comprising a seal ring, a flexible member (also not shown) and an outside seal member or crown 16.

The header 30 has a transverse inlet bore 19 extending transverse the longitudinal axis "A" of the bowl and then into a longitudinal passageway coupled to the inner bore of the feed tube assembly. The passageway leads to stem 18 forming an inlet fluid communication path for feed fluid, i.e., whole blood or saline, to enter the interior of centrifuge bowl body 12 at the lower longitudinally axial portion 12L of the bowl body 12.

Header 30 is also provided with a transverse outlet bore 20, which extends transversely into a peripheral channel extending in parallel relationship with the feed tube assembly and into an outlet coaxial passageway (not shown). A secondary shield 32 is formed on header 30 and extends over the rotary seal. A pair of complementary skirts 21 and 23 provide an effluent passageway, therebetween, connecting the outlet passageway to the outlet bore 20.

Internal screw threads, on seal crown 16, secure the seal and header assembly to complementary threads on the bowl body.

The bowl body 12 is preferably an integral body adapted to be manufactured by blow molding or injection blow molding and may be formed of a suitable plastic, such as transparent styrene or equivalent.

The bowl body is formed of an upper ring portion 12R, an upper diagonal portion 12U extending radially outwardly and inclined downwardly, a straight middle central portion 12C extending vertically downward, a lower diagonal portion 12D extending radially inwardly and downward, and a lower cross portion 12L. Screw threads are formed on the outer surface of ring portion 12R and an opening extends longitudinally from the inner surface of the ring portion 12R into the main portion of the bowl body 12. An optional groove is formed about the periphery of the bowl at 12G to form a holding surface for a centrifuge rotor chuck (not shown).

Prior to inserting the header and seal assembly 28 into the bowl body, a core assembly consisting of core body 8 and diverter 6 is inserted into the interior of the bowl.

The core body is adapted to be inserted into the bowl body 12 through the opening in ring portion 12R. Core body 8 is an integral member formed of a suitable rigid, or semi-rigid, blood compatible transparent plastic and has a cylindrical outer wall 8B extending longitudinally downward and coaxial to the axis A of bowl body 12. An upper transverse ring portion 8A of core body 8 is adapted to abut the inner wall of the ring portion 12R of the bowl body 12 when the core body is inserted into the upper opening of the bowl body 12.

Four L-shaped reinforcing tabs (not shown) are formed on the top wall of core body 8 to reinforce the ring portion 8A. Four peripheral slots (one of which is shown at 4) extend along the periphery of the core body at the juncture between the ring portion 8A and the cylindrical outer wall 8B. These slots provide a passageway for the exit of effluent, such as supernatant or plasma, which has been separated from the packed red blood cells by the operation of the centrifuge cell washing or pheresis process within the bowl body 12.

A coaxial opening 50 is provided in the transverse ring 8A of core body 8B to enable feed tube stem 18 to pass unimpeded into the lower portion 12L of the bowl body.

Diverter 6 is a donut-like member formed of blood-compatible semi-rigid transparent plastic material. The diverter has an outside diameter greater than the diameter of the opening in the top of the bowl body 12 and is provided with scalloped openings 22 at the peripheral edge thereof. The outer diameter of the diverter is about equal to the inner diameter of the bowl body at the mid-section 12C, so that when the diverter is folded and inserted into the bowl body through the top opening and unfolded into its flat aspect horizontal position, it extends across the entire cross-section of the bowl at the mid-section 12C. The core body is then inserted through the opening. The length of the cylindrical longitudinal wall 8B is just sufficient so that when the core body 8 is fully inserted and cover 16 is screwed in place, the diverter 6 is pushed into a horizontal position vertically aligned with the start of the lower radially inwardly diagonal or inclined portion 12D of the bowl.

In this manner, the diverter 6 is retained in a slightly bowed compressed rigid position at the precise vertical location preferred for introduction of fluid to the separation region "S" between the mid-section bowl wall 12C and the core body wall 8B.

Optionally, a ring of openings 2 are provided intermediate central opening 14 and the peripheral scalloped openings 22 at the periphery of the diverter 4. As fluid, such as anticoagulated shed blood, is first introduced to the bowl, it enters at the bottom region adjacent wall 12L and under the influence of centrifugal force, flows outwardly and upwardly in the direction of the arrows and enters the separation region S at the periphery thereof through scalloped openings 22.

Eventually, a layer of more dense packed red blood cells accumulates at the outermost radius of the separation region, covering the peripheral openings 22.

As wash fluid is next introduced, it is easier for this fluid to enter the separation region S at the radially inward openings 2 than at the peripheral openings 22. In this way, a desirable cell washing cross-flow is established with cell washing fluid flowing generally upwardly from openings 2 while whole blood particulate is in suspension sediment travelling in a radially outward direction.

Figure 3:
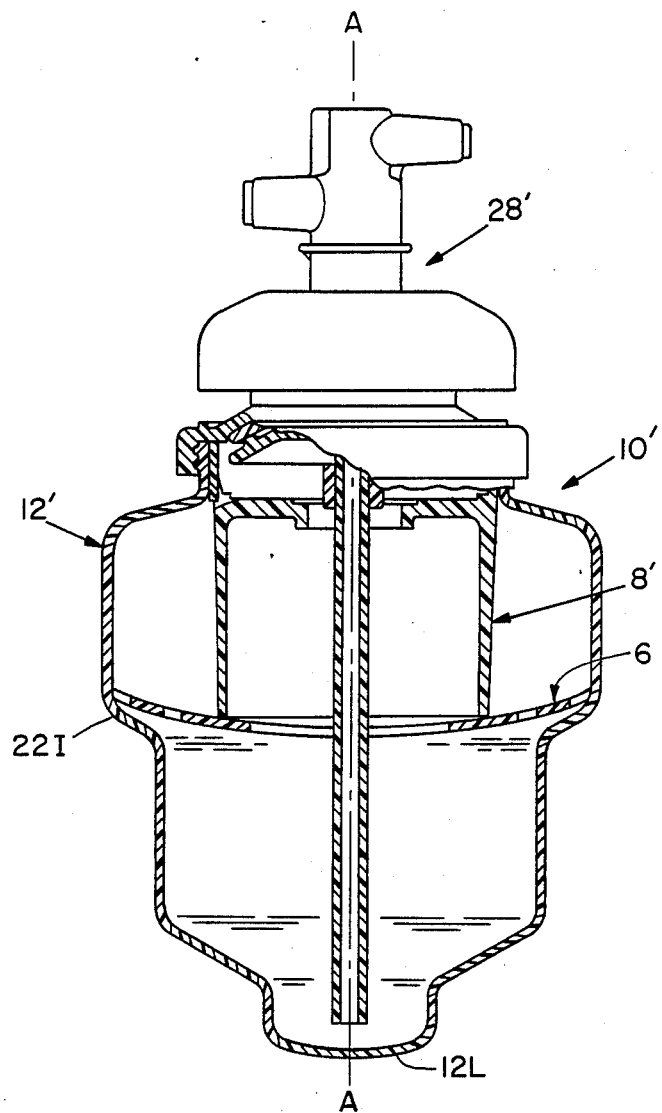
FIG. 3 is a view as in FIG. 1 except that a smaller volume bowl body and shorter length core is employed.

FIG. 3 shows an alternate embodiment of the disposable centrifuge bowl 10' of the invention in which a smaller volumetric size bowl 12' is utilized in conjunction with a shorter length core body 8'. The bowl body is substantially as described in co-pending design patent application, Ser. No. 07/102,646 filed Sep. 30, 1987 to Thomas D. Headley entitled "Bowl Body".

In this bowl body, the outer diameter of the mid-section of the bowl 12' is stepped from a relatively large diameter equal to the diameter of the mid-section in FIG. 1 to a lesser diameter at a point about halfway along the length thereof. The length of the core 8' is similarly foreshortened, so that when the core is inserted against diverter 6', the diverter is compressed at the beginning of the first diagonal inwardly inclined region 12I of the bowl body.

The diverter 6' may be identical in size and shape to the above previously described diverter 6, in all respects, yet function in a similar manner in the smaller size bowl.

EQUIVALENTS

Those skilled in the art will recognize that there are many equivalents to the specific embodiments shown herein. Accordingly, the invention is not to be limited except as may be required by the scope of the claims herein.

We claim:

1. A disposable blood processing centrifuge rotor comprising:
   (a) a rotatable bowl body having at least one straight section and upper and lower inclined diagonal sections connected to one of said straight sections; said body being rotatable about an axis and having a single aperture therein concentric with said axis through an outer wall of the bowl body; and
   (b) a rotary seal assembly affixed to said bowl body and covering said aperture and having input and output ports for fluid communication with the interior of said bowl body;
   (c) a core assembly comprising:
      (i) a walled core body having a transverse ring portion which mates with the bowl body at the aperture thereof and a cylindrical portion longitudinally extending from said ring portion; and
      (ii) a diverter member having a donut-like shape with an inner opening coaxial to said axis and a diameter smaller than the outer diameter of said cylindrical portion and an outer apertured periphery with a diameter about equal to the inner diameter of said straight section and larger than the diameter of the bowl aperture and sufficiently non-rigid as to be capable of being inserted through said bowl aperture and be rigidly retained in a horizontal position against an inner wall of the bowl body by compression as the bottom of the cylindrical portion of said core body abuts the diverter member.

2. The rotor of claim 1 wherein the aperture is on the top of the bowl body and the upper section of the bowl body inclines radially outwardly from top to bottom while the lower section of the bowl body inclines radially inwardly from top to bottom and the diverter member is retained against the bowl body at a region where the bowl body begins to incline radially inwardly.

3. The rotor of claim 2 wherein the bowl body has upper and lower straight sections and the diverter is retained between the upper and lower straight sections.

4. The rotor of claim 1 wherein the outer apertures at the periphery of the diverter member are in the form of scalloped edges.

5. The rotor of claim 1 wherein a plurality of openings are formed in said diverter member radially intermediate said apertured periphery and said inner opening to permit fluid from below said core body to enter the interior of said bowl body between said cylindrical portion and said straight section.

6. A disposable blood processing centrifuge rotor comprising:
   (a) a bowl body rotatable about its longitudinal axis and having a single closeable bowl body aperture concentric with said axis at one end thereof and an interior wall;
   (b) a core assembly concentric with said axis and having an open center extending within said bowl from said aperture about said axis formed of a cylindrical wall member extending longitudinally to an apertured disc-like diverter which is held across said bowl body at a location corresponding to the length of said wall member when fully inserted in the bowl body by being compressed by said wall member against said interior wall; and
   (c) a rotary seal assembly having a cover for sealing said seal assembly to the outer body wall about the periphery of said single aperture.

7. The rotor of claim 6 wherein the diverter is at least partly flexible at portions having an outer diameter greater than the bowl body aperture.

8. A disposable centrifuge blood processing rotor comprising:
   (a) a bowl body comprising a walled structure with an inner surface adapted for rotation about its longitudinal axis and having a bowl body aperture, through said structure, to the interior of said bowl body and concentric with said axis at one end of the walled structure of the bowl body;
   (b) a core assembly comprising a core body and a disc-like diverter with a central opening, and peripheral apertures, said assembly being insertable in said bowl body aperture and said diverter being retained by said core body pushing against said diverter which diverter is disposed horizontally across the interior of said bowl body thereby compressing the diverter; and
   (c) a rotary seal assembly affixed to the outer wall about the periphery of said aperture and having an effluent port and an input port in fluid communication with the interior of said bowl body.

9. The rotor of claim 8 wherein the diverter has an outer diameter when flat which exceeds the diameter of the bowl body aperture and is sufficiently flexible as to be capable of insertion through said aperture, yet sufficiently rigid as to be retained, by longitudinal force of said core body, across the interior of said bowl body at a region where said bowl body inclines radially inwardly from top to bottom.

10. The rotor of claim 9 wherein the diverter has a ring of openings intermediate the central opening and peripheral apertures.

* * * * *